United States Patent
Dreyer et al.

(10) Patent No.: US 8,746,071 B2
(45) Date of Patent: Jun. 10, 2014

(54) APPARATUS FOR DETERMINING AND/OR MONITORING A PROCESS VARIABLE

(75) Inventors: Volker Dreyer, Lörrach (DE); Sergej Lopatin, Lörrach (DE); Oliver Schmidt, Hausach (DE)

(73) Assignee: Endress + Hauser GmbH + Co. KG, Maulburg (DE)

( * ) Notice: Subject to any disclaimer, the term of this patent is extended or adjusted under 35 U.S.C. 154(b) by 463 days.

(21) Appl. No.: 13/129,124

(22) PCT Filed: Oct. 27, 2009

(86) PCT No.: PCT/EP2009/064130
§ 371 (c)(1),
(2), (4) Date: May 24, 2011

(87) PCT Pub. No.: WO2010/054931
PCT Pub. Date: May 20, 2010

(65) Prior Publication Data
US 2011/0226064 A1    Sep. 22, 2011

(30) Foreign Application Priority Data
Nov. 14, 2008   (DE) .......................... 10 2008 043 764

(51) Int. Cl.
*G01N 29/028*   (2006.01)
*G01N 29/22*   (2006.01)

(52) U.S. Cl.
USPC ............................................... 73/627; 73/632

(58) Field of Classification Search
USPC ......................................... 73/632, 32, 290 V
See application file for complete search history.

(56) References Cited

U.S. PATENT DOCUMENTS

| | | | |
|---|---|---|---|
| 4,594,584 A | 6/1986 | Pfeiffer et al. | |
| 6,389,891 B1 * | 5/2002 | D'Angelico et al. | 73/290 V |
| 6,644,116 B2 * | 11/2003 | Getman et al. | 73/290 V |
| 7,043,981 B2 * | 5/2006 | Kuhny et al. | 73/290 V |
| 7,681,445 B2 * | 3/2010 | Pfeiffer | 73/290 V |
| 8,220,313 B2 * | 7/2012 | Lopatin et al. | 73/32 R |
| 2004/0056612 A1 | 3/2004 | Kuhny et al. | |
| 2004/0078164 A1 * | 4/2004 | Lopatin et al. | 702/100 |

FOREIGN PATENT DOCUMENTS

| | | |
|---|---|---|
| DE | 10 2004 033 311 A1 | 1/2006 |
| GB | 2 351 805 A | 1/2001 |

OTHER PUBLICATIONS

English translation of the international Preliminary Examination Report.

* cited by examiner

*Primary Examiner* — J M Saint Surin
(74) *Attorney, Agent, or Firm* — Bacon & Thomas, PLLC

(57) ABSTRACT

An apparatus for determining and/or monitoring a process variable. The apparatus includes a housing, a mechanically oscillatable unit, and a transducer unit, which is arranged and clamped between two housing elements in such a manner that a predeterminable pressure acts on the transducer unit along an imaginary axis. An equalizing element is provided, whose coefficient of thermal expansion and/or height are/is selected in such a manner that a temperature-related expansion of the equalizing element during a temperature-related expansion of a housing element to be compensated leads to the pressure acting on the transducer unit being greater than or equal to a predeterminable prestress limit value.

10 Claims, 5 Drawing Sheets

APPARATUS FOR DETERMINING AND/OR MONITORING A PROCESS VARIABLE

TECHNICAL FIELD

The invention relates to an apparatus for determining and/or monitoring at least one process variable of a medium. The apparatus includes: at least one housing; at least one mechanically oscillatable unit; and at least one transducer unit, which excites the mechanically oscillatable unit to execute mechanical oscillations and which receives mechanical oscillations from the mechanically oscillatable unit; wherein the transducer unit is arranged and clamped between at least two clamping elements of the housing in such a manner that, at least along an imaginary axis, a predeterminable pressure acts on the transducer unit. The process variable is, for example, fill level, density or viscosity of a medium, which is, for example, a liquid, a gas or a bulk good.

BACKGROUND DISCUSSION

In the state of the art, for determining fill level and other process variables of a medium, so called oscillatory forks (e.g. EP 0 444 173 B1), single rods (e.g. WO 2004/094964 A1) and also membrane oscillators are known. Exploited in the respective measurements is the fact that the characterizing variables of the mechanical oscillations (oscillation amplitude, resonance frequency, phase difference over frequency) of the oscillatable unit depend on the contact with the medium and also on the properties of the medium. Thus, for example, frequency or amplitude of the oscillations decreases when especially a liquid medium reaches and at least partially covers the oscillatable unit. The liquid medium acts on the oscillating body of the sensor—i.e. on, for example, the oscillatory fork, or the single rod, or the membrane, as the case may be—and does so, on the one hand, as extra mass moved along with the oscillating body of the sensor, so that the oscillation frequency sinks, and, on the other hand, as a mechanical damper, so that the oscillation amplitude decreases. Therefore, from the decrease in the oscillation frequency or the amplitude, it can be ascertained that the medium has reached a fill level dependent on the physical form and on the position of mounting of the apparatus. Furthermore, the oscillation frequency is dependent also, for example, on the viscosity of the medium (see e.g. EP 1 325 301).

The previously described sensors are frequently used as limit level switches. If the process variable is, for example, fill level, the sensor then produces a signal, which shows that the fill level, which is predetermined by the physical form of the sensor and its location of mounting, was reached or subceeded (fallen beneath).

Such mechanical, or vibronics-based, limit level switches or measuring devices for liquids and bulk goods usually make use of a mechanical resonator (the oscillatable unit) and a drive. The resonator determines the resonance properties of the sensor and reacts to the medium with a frequency change and/or with an amplitude change. The drive produces the mechanical oscillations in the resonator, and serves as a feedback element for the electronics which electrically controls the sensor. Thus, the designations "drive" and "transducer" unit can essentially be used synonymously.

The drives most often make use of piezoelectric elements in the form of stacked disks or rings. Such piezoelements are made, for example, of ceramic lead-zirconate-titanate (LZT). In given cases, ceramic insulating discs are also provided, which galvanically isolate the piezoelements from the housing. For such piezo drivers, a mechanical prestress is required, which serves for the force-based (e.g. frictional) connection of the transducer unit with a mechanical resonator, i.e. with the mechanically oscillatable unit. If the mechanical prestress gives way or is no longer high enough, the sensor can stop working and, for example, no longer produce switching signals. Therefore, in the specification region of the sensor, the mechanical prestress must remain within certain limits.

Typical drives for vibratory limit switches are described, for example, in the following documents: DE 1773 815, DE 3348 119, DE 4118 793, DE 39 31453, DE 1002 3302, DE 42 01360, DE 10 2004 009 495, DE 10 2006 046 251, DE 103 21 025, DE 101 29 556 or EP 1 134 038.

Especially critical is the temperature behavior of a piezo stack drive. The ceramic materials generally have markedly smaller coefficients of thermal expansion than the steel alloys which are used for the housing surrounding the stack drive and, for example, also the feedback electronics. In the case of increased temperatures, a metal sensor housing and the metal securement elements expand to a greater extent than the ceramic in the piezo-stack. This leads to a relaxing of the drive and, as a result, to sensor failure.

The transducer unit is, in such case, prestressed against a membrane in the direction of the medium or the process. In such case, the membrane is, for example, the mechanically oscillatable unit itself, or, for example, the two fork tines of an oscillatory fork are secured to the unit.

In a variant, via the use of the spring properties of the membrane, it is possible to hold the prestress in the drive approximately constant in specific temperature ranges. This functions well, for example, in a temperature range of −40° C. to 150° C. for particular membranes with a diameter greater than 30 mm and a thickness of, for instance, 1 mm.

SUMMARY OF THE INVENTION

An object of the invention is to provide a measuring device, in the case of which the mechanical prestress essentially remains preserved at high temperatures.

The invention achieves the object by features including that at least one equalizing element is provided, wherein the coefficient of thermal expansion of the equalizing element and/or the height of the equalizing element along the imaginary axis are/is selected in such a manner that a temperature-related expansion of the equalizing element along the imaginary axis during a temperature-related expansion (along the imaginary axis) of a housing element to be compensated leads to the fact that pressure acting along the imaginary axis on the transducer unit is essentially greater than or equal to a predeterminable prestress limit value, and wherein the temperature-related expansion (along the imaginary axis) of the housing element to be compensated affects distance along the imaginary axis between two housing elements, between which the transducer unit is arranged and clamped. The sensor of the invention thus includes an equalizing element, which expands under the influence of temperature and assures that pressure bearing on the transducer unit, and, associated therewith, the prestress, does not fall beneath a limit value.

in other words: due to a temperature change and the expansion behavior of the housing associated therewith, there results a change in the distance between two housing elements serving for the prestress of the transducer unit. Since the material of the transducer unit has a different temperature coefficient, the transducer unit displays different expansion behavior. Due to this, in the state of the art, it can occur that, after a temperature change, the transducer unit is, for a certain period of time, no longer prestressed, since the distance between the housing elements serving for the clamping is too large for the-not yet matching-length change of the transducer unit. According to the invention, the equalizing element displays an expansion behavior of such a sort, that it virtually adjusts the transducer unit to the expansion of the housing, and therewith to the changed distance between the housing elements. In such case, the expansion of a particular housing element is especially to be compensated. This is the element which especially determines the distance between the elements serving for the clamping. In such case, the element to be compensated can be identical with one of the elements serving for the clamping, a part thereof or a supplemental element.

In the state of the art, the problem to be solved thus resides in the fact that the housing—or the section or the element of the housing, which defines the distance between the two elements, between which the transducer unit is clamped—expands faster under the action of temperature than the elements of the transducer unit, i.e. especially faster than the elements composed of a ceramic, such as, for example, the piezoelectric elements of the transducer unit. The equalizing element compensates for this different expansion behavior and virtually assures that the transducer unit is matched to this expansion change. For such purpose, the equalizing element is to be formed from a suitable material of suitable dimensions.

An embodiment provides that the coefficient of thermal expansion of the equalizing element and/or the height of the equalizing element along the imaginary axis are/is selected in such a manner, that the temperature-related expansion of the equalizing element along the imaginary axis is essentially equal to the temperature-related expansion (along the imaginary axis) of the housing element to be compensated.

An embodiment includes that the coefficient of thermal expansion of the equalizing element is essentially equal to or greater than the coefficient of thermal expansion of the housing element to be compensated.

An embodiment provides that the transducer unit is arranged and clamped along a bolt between a membrane and a nut or between a bearing region and a nut, and that the housing element to be compensated is the bolt. The transducer unit preferably includes, in such case, piezoelectric elements, which, for example, are arranged on the bolt in the form of rings.

An embodiment includes that the transducer unit is arranged and clamped between a membrane and a yoke, and that the housing element to be compensated is a housing section between the membrane and a bearing of the yoke on the housing parallel to the imaginary axis. The transducer unit is, in such case, especially embodied in the manner of a monolithic block.

An embodiment provides that the equalizing element is arranged along the imaginary axis between the at least two housing elements, between which the transducer unit is arranged.

An embodiment includes that the height of the equalizing element along the imaginary axis is essentially given by the following formula:

$$HE = HT * \frac{\alpha 1 - \alpha T}{\alpha E - \alpha 1}.$$

In such case, HE is the height of the equalizing element along the imaginary axis, HT is the height the transducer unit along the imaginary axis, α1 is the coefficient of thermal expansion of the housing element to be compensated, αT is the coefficient of thermal expansion of the transducer element, and αE is the coefficient of thermal expansion of the equalizing element.

An embodiment provides that the transducer unit is embodied as a stack, which has at least one piezoelectric element.

An embodiment includes that at least one insulating element is provided. This insulating element is, for example, a component of the transducer element, and/or the insulating element is, for example, arranged between the transducer element and the membrane. The insulating element, which serves, for example, for galvanic isolation, is, in such case, especially likewise arranged between the at least two housing elements serving for the clamping.

An embodiment provides that the transducer unit has at least one soldering tab.

An embodiment includes that the height of the equalizing element along the imaginary axis is given essentially by following formula:

$$HE = \frac{(HP + HI + HS) * \alpha 1 - (HP * \alpha P + HI * \alpha I + HS * \alpha S)}{\alpha E - \alpha 1},$$

in such case, HE is the height of the equalizing element along the imaginary axis, HP is the height of the at least one piezoelectric element along the imaginary axis, HI is the height of the at least one insulating element along the imaginary axis, HS is the height the at least one soldering tab along the imaginary axis, α1 is the coefficient of thermal expansion of the housing element to be compensated, αP is the coefficient of thermal expansion of the at least one piezoelectric element, αI is the coefficient of thermal expansion of the at least one insulating element, αS is the coefficient of thermal expansion the at least one soldering tab, and αE is the coefficient of thermal expansion of the equalizing element.

The mechanically oscillatable unit is, for example, an oscillatory fork, a single rod or a membrane capable of a bending mode, wherein the process variable is, for example, the fill level, the density or the viscosity of a medium, which is, for example, a liquid or a bulk good.

BRIEF DESCRIPTION OF THE DRAWINGS

The invention will now be explained in greater detail on the basis of the appended drawing, the figures of which show as follows.

DETAILED DISCUSSION IN CONJUNCTION WITH THE DRAWINGS

Figure 1:
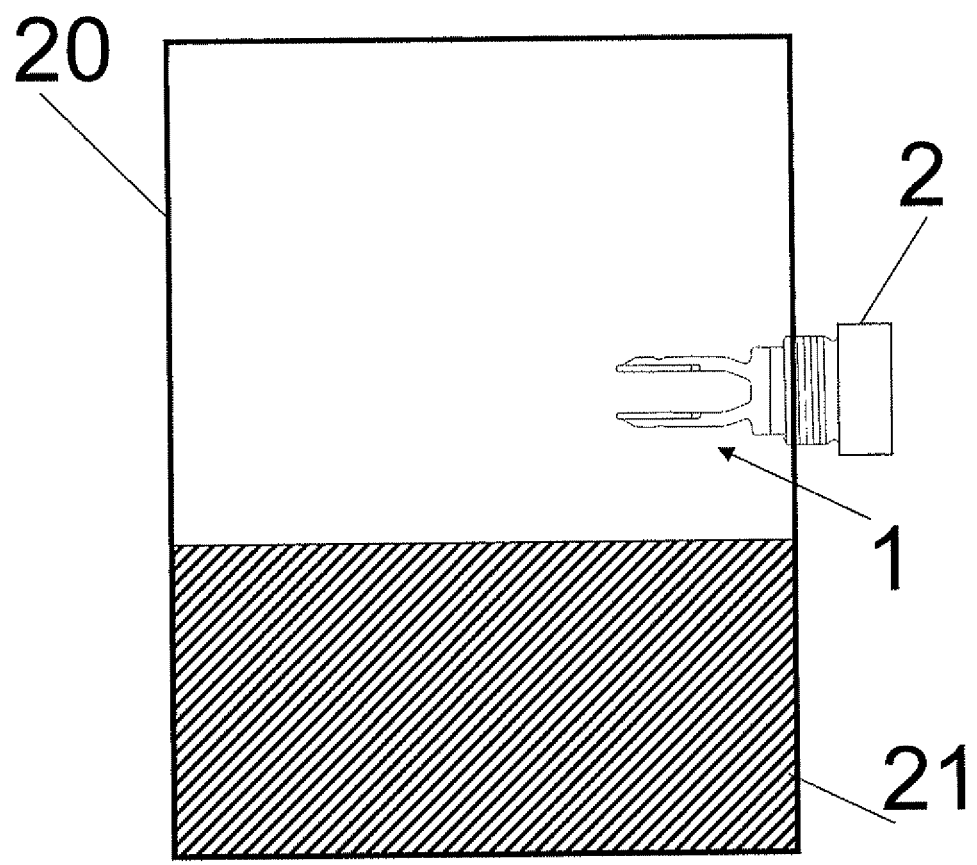
FIG. 1 is a schematic representation of the application of a measuring device of the invention.

FIG. 1 shows an example in which a sensor is used as a limit level switch. The mechanically oscillatable unit 1 is, in such case, a so-called oscillatory fork, i.e. two fork tines are secured on a membrane. The fork tines reach into the inner space of the container 20, within which is located the medium 21, which is, for example, a liquid, but can, however, also be a bulk good. If the medium 21 reaches the mechanically oscillatable unit 1, it then influences the oscillations, as is evidenced, for example, in a change in the frequency and/or the amplitude. In such case, the interaction between the medium 21 and oscillatable unit 1 also permits, for example, the determining or monitoring of such process variables as density or viscosity, wherein, in the case of these measurings, the degree of covering by the medium should be known.

Located outside of the container 20 here is also the housing 2, in which is located the transducer unit, and, for example, also the electronics, which is responsible for the feedback and for the processing of the oscillations.

Figure 2:
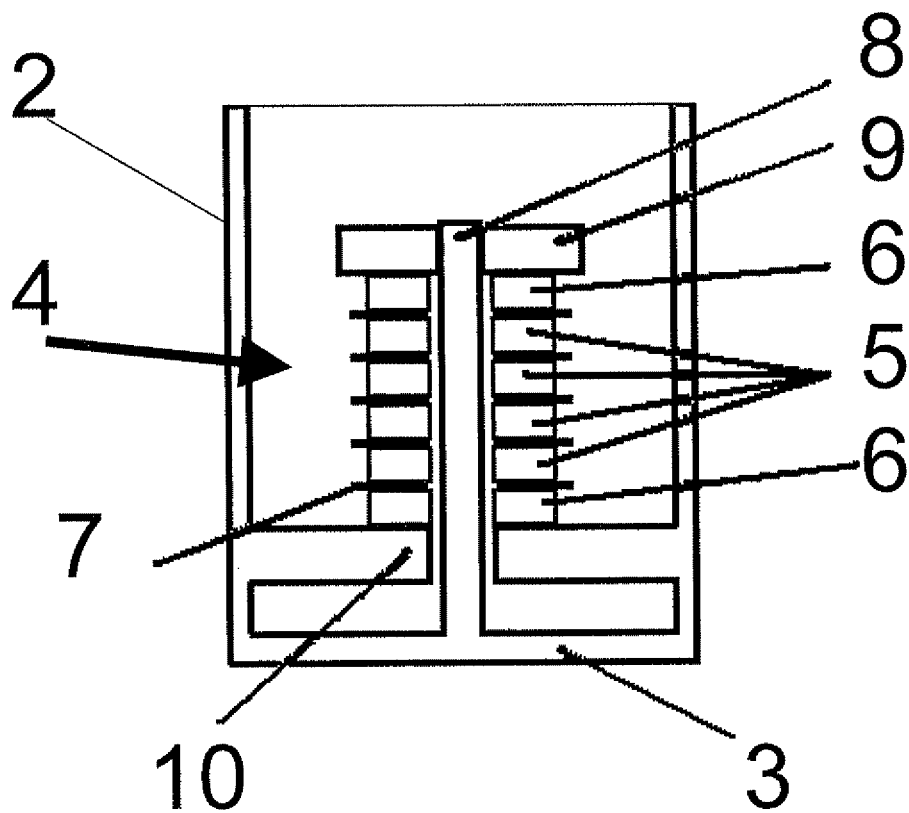
FIG. 2 is a schematic representation of a part of a sensor according to the state of the art in a first variant.
Figure 3:
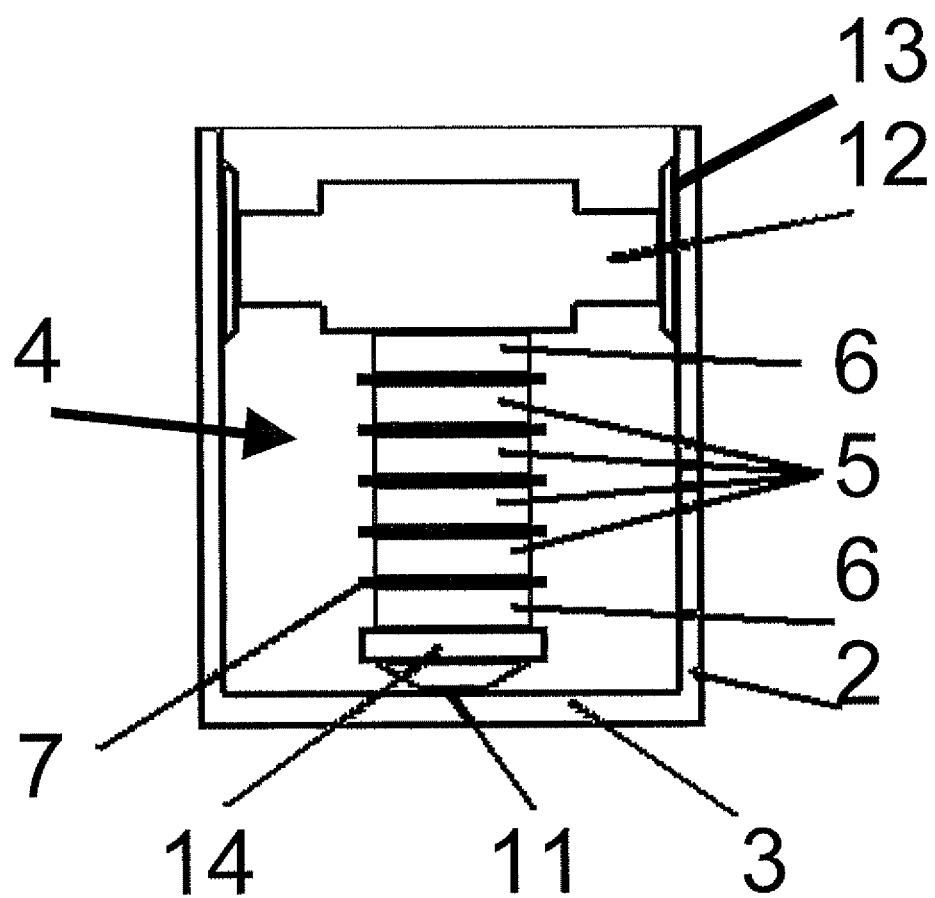
FIG. 3 is a schematic representation of a part of a sensor according to the state of the art in a second variant.
Figure 4:
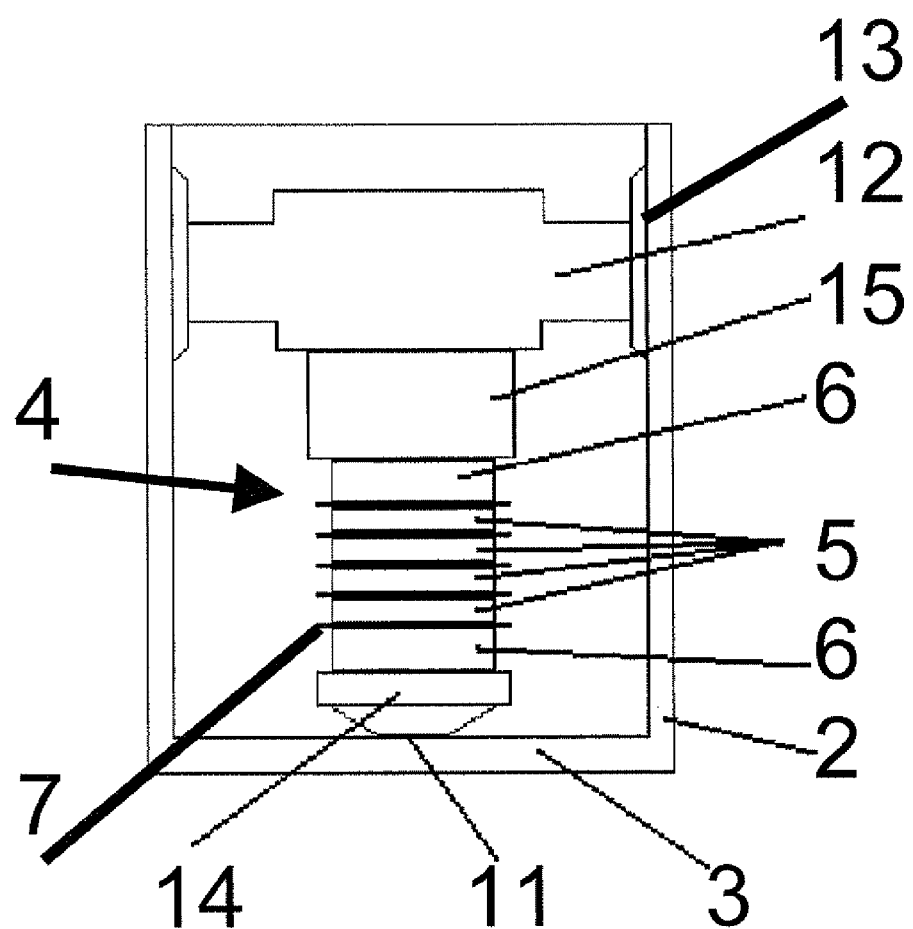
FIG. 4 is a schematic representation of a part of an sensor of the invention in reference to the second variant of FIG. 3.
Figure 5:
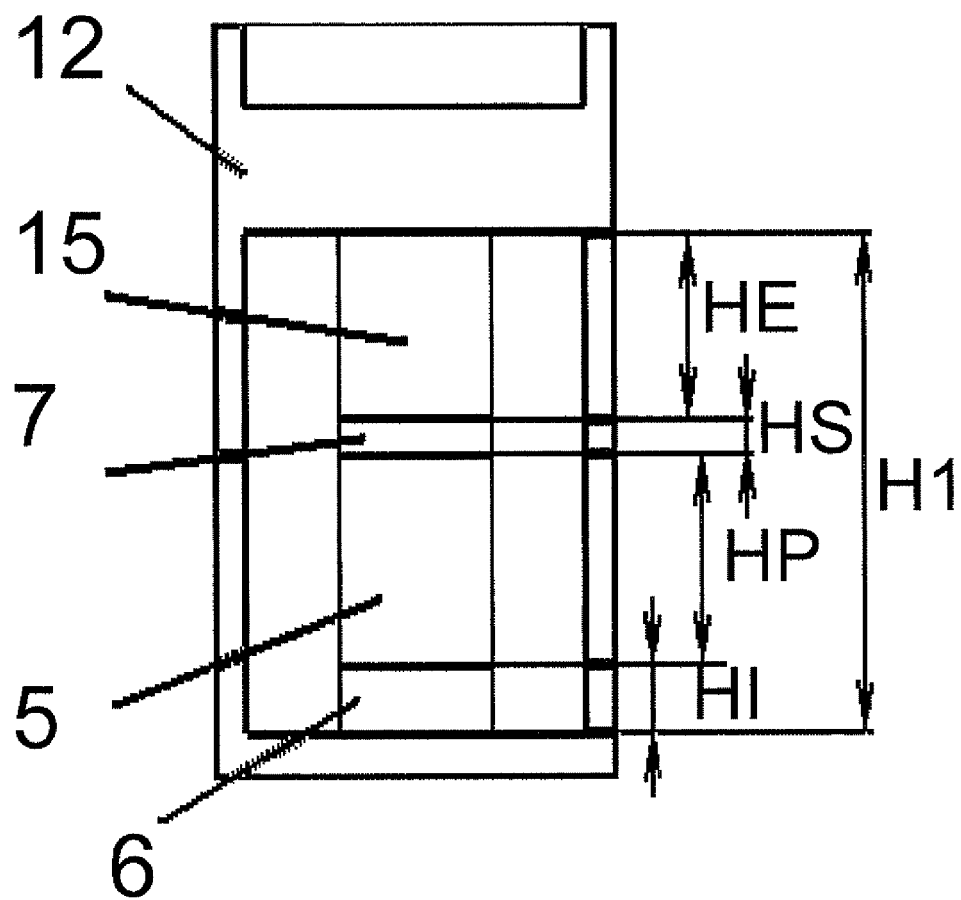
FIG. 5 is a representation of FIG. 4 with simplifications for the calculation of the arising variables.

FIGS. 2 and 3 show two typical designs of piezo drivers for vibration sensors. These sketches schematically show the most important design elements of the drive environment. Of the mechanically oscillatable unit, in each case, here, only a membrane 3 is presented, which can itself be the oscillatable unit (e.g. as a bending modes resonator), or on which the fork tines of the oscillatory fork are mounted. The oscillatable unit can, moreover, also be a so-called single rod. Thus, essentially, only the fundamental principle is shown here: The transducer unit 4 is located within the housing 2 and is pressed against a part of the housing 2, in order that the required prestress produced by the applied pressure be given. Shown in these, and also in the other illustrations, FIGS. 4 and 5, is, in each case, a section through the—for example, rotationally symmetric and thus also pot-shaped—housing 2.

In FIG. 2, a construction of a transducer unit 4 with piezoelectric elements in the form of ceramic rings is to be seen. The annular piezoelectric elements 5 and insulating elements 6 are stacked with soldering tabs 7 onto a standing bolt 8 and clamped together relative to the bearing region 10 with a nut 9. The membrane 3 and the bearing region or bearing plate 10 form a spring element for the transducer unit 4—here essentially embodied as a piezo-stack—wherein this spring element conducts the required mechanical prestress into the housing 2.

FIG. 3 shows the drive structure with a point of securement 11 on the membrane 3 and a yoke 12, which rests on a seating area, or bearing region 13, of the sensor housing 2. The transducer unit 4 is embodied, in such case, as a monolithic block with disk-shaped piezoelectric elements 5, disk-shaped insulating elements 6, as well as the individual soldering tabs 7. The transducer unit 4 rests, in such case, a metal nipple 14 on the membrane 3, and is, as a whole, prestressed between the membrane 3 and the yoke 13, wherein the membrane 3 also serves in this construction as a spring element.

The two structural types from the state of the art in FIG. 2 and FIG. 3 make necessary a high mechanical prestress in the piezo drive, or transducer unit, 4, wherein the prestress is determined by a spring element, here in the form of the membrane 3 (FIG. 3) or the combination of the membrane 3 and the bearing region 10 (FIG. 2). The prestress is typically set with a bolt 8, a set screw or a nut 9, i.e., a certain pressure is usually set during manufacturing, which effects the desired prestress. In such case, it should be assured that the membrane 3 and other securement elements, e.g. the yoke 12, are not mechanically overloaded. If the mechanical stress in the affected parts exceeds the respective yield point, the metal parts will be plastically deformed, which can bring about sensor failures.

Especially critical is the temperature behavior of the piezo stack drive 4. The ceramic materials usually have markedly smaller coefficients of thermal expansion than the steel alloys which are used for the housing 2, or, for example, for the bolt 8. In the case of increased temperatures, a metal sensor housing and the metal securement elements expand to a greater degree than the ceramic in the piezo stack. This leads to a reduction in the prestress. This effect is especially noticeable in the case of the variant with a standing bolt (FIG. 2) when an external pressure is present, since the external pressure leads to an additional relaxing of the drive.

In the illustrations of FIGS. 4 and 5, the solution of the invention is shown.

The invention addresses the loss of the mechanical prestress in a piezo drive in the case of high temperatures of up to 400° C. The goal, in such case, is achieved by a supplemental structural element in the form of an equalizing element. The structural element has the shape of a ring, a disk or a strap, and is, in such case, made of a material, which preferably has a high coefficient of thermal expansion (CTE). In such case, the CTE of the structural element should be larger than the CTE of the material of the housing or the bolt, depending on which is responsible for the clamping and for producing the prestress.

In other words: The transducer unit is clamped between two elements (in FIG. 2 this is the nut 9 and the bearing region 10, and in FIG. 3, the yoke 13 and the membrane 3) in such a manner, that a pressure bears on the transducer unit along an imaginary axis (in the case of FIG. 2 and FIG. 3 this is, in each case, the perpendicular to the plane of the membrane), this pressure corresponding to a prestress predeterminable during manufacture. Additionally, according to the invention, an equalizing element is provided, whose CTE is at least greater than the CTE of the ceramic elements of the transducer unit. The pressure on the transducer unit is especially dependent on the distance along the imaginary axis between the two elements between which the transducer unit is clamped. This distance can change due to temperature, and in the case of a rising temperature, can especially become larger. Essential sections in such case are, for example, the bolt 8 of the variant of FIG. 2, or the housing section between the membrane 3 and the seat 13 of the yoke 12 of the variant of FIG. 3. In order to maintain the prestress, the CTE of the equalizing element should, consequently, be at least equal to, or greater than, the CTE of those elements to be compensated, i.e. the respective housing components (e.g. bolt or housing elements).

FIG. 4 shows the variant of FIG. 3 having an equalizing element 15 for compensating for differences between the thermal expansion of the housing 2 and the ceramic disks of the transducer unit 4. The equalizing element 15 can also be made from a material with an increased CTE, as well as from a stainless steel. In such case, the compensation effect need not necessarily be complete; in given cases, it is sufficient when the pressure bearing on the transducer unit 4 does not fall beneath a minimum required prestress limit value. As a function of the embodiment of the membrane 3 and its elastic properties, interactions will also occur which likewise can have a positive effect on the prestress.

FIG. 5 shows a simplified representation of the structure of FIG. 4. Here, for calculating the size relationships, the piezoelectric elements, the insulating elements and the soldering tabs were, in each case, consolidated to a single element.

In total, there results: One block of piezoelectric ceramic 5 of height HP (corresponding to the total height of all piezo discs used in the transducer unit) and CTE $\alpha P$; one block of insulating ceramic 6 of height HI (corresponding to the total height of all insulating discs) and CTE $\alpha I$; one block of, for example, bronze or brass 7 of height HS (corresponding to the total height of all soldering tabs) and CTE $\alpha S$; and, finally, one block of equalizing element 15 of height HE and CTE $\alpha E$.

The equalizing element 15 can, in such case, also comprise a plurality of disks or rings.

These blocks should, in the ideal case, have a thermal expansion equal to the thermal expansion of the height H1 of the housing between the membrane and bearing location of the yoke 12. The material of the housing should, in such case, have the CTE $\alpha 1$.

As regards the expansion as the product of height and CTE, it should thus hold that the expansion of the housing is equal to the sum of the individual expansions of the blocks. Thus: $H1*\alpha 1 = HP*\alpha P + HI*\alpha I + HS*\alpha S + HE*\alpha E$ For the individual heights, as a starting condition, it is furthermore true that: $H1=(HP+HI+HS+HE)$ Therewith, there then results for the required total height of the equalizing element:

$$HE = \frac{(HP+HI+HS)*\alpha 1 - (HP*\alpha P + HI*\alpha I + HS*\alpha S)}{\alpha E - \alpha 1}$$

Thus, depending on the construction of the transducer unit and the type of housing, or the element to be compensated, the optimal height for a complete equalization can be calculated. If the discussed prestress limit value is sufficient, one should dimension corresponding to this.

An example is a piezo drive of six piezo discs, each 0.5 mm in height; two insulating discs of aluminum oxide, each 2 mm thick; and seven soldering tabs of bronze, each 0.15 mm thick. The sensor housing is composed, in such case, of stainless steel 1.4435 (316L).

In order to compensate for a thermal expansion of up to 300° C., an aluminum alloy or a magnesium alloy would come into question for the equalizing element. The associated CTE values are $26*10^{-6}*1/°$ C. for the aluminum alloy and $28*10^{-6}*1/°$ C. for the magnesium alloy.

There results therewith for the height of the equalizing element 7.66 mm for the aluminum alloy and 6.27 mm for the magnesium alloy.

The calculated heights for the equalizing element correspond, in such case, to the optimal, i.e. essentially complete, compensation. The piezo drivers expanded with such an equalizing element have a stable mechanical prestress, which is almost independent of temperature. In this way, safety and reliability of the sensor can clearly be improved over a broad temperature range.

The invention claimed is:

1. An apparatus for determining and/or monitoring at least one process variable of a medium, comprising:
   at least one housing;
   at least one mechanically oscillatable unit;
   at least one transducer unit, which excites said at least one mechanically oscillatable unit to execute mechanical oscillations, and which receives mechanical oscillations from said at least one mechanically oscillatable unit; and:
   at least one equalizing element, wherein:
   said at least one transducer unit is arranged and clamped between said at least two clamping elements of said at least one housing in such a manner that, at least along an imaginary axis, a predeterminable pressure acts on said at least one transducer unit;
   a coefficient of thermal expansion of said at least one equalizing element and/or a height of said at least one equalizing element along the imaginary axis are/is selected in such a manner that a temperature-expansion of said at least one equalizing element along the imaginary axis during a temperature-related expansion (along the imaginary axis) of a housing element to be compensated leads to the fact that pressure acting along the imaginary axis on said transducer unit is essentially greater than or equal to a predeterminable prestress limit value;
   the temperature-related expansion (along the imaginary axis) of said housing element to be compensated affects distance along the imaginary axis between two housing elements, between which said at least one transducer unit is arranged and clamped; and
   the coefficient of thermal expansion of said at least one equalizing element and/or height of said at least one equalizing element along the imaginary axis are/is selected in such a manner that temperature-related expansion of said at least one equalizing element along the imaginary axis is essentially equal to temperature-related expansion (along the imaginary axis) of said housing element to be compensated.

2. The apparatus as claimed in claim 1, wherein:
   said at least one transducer unit is arranged and clamped lengthwise of a bolt between a membrane and a nut or between a bearing region and a nut; and
   the housing element to be compensated is said bolt.

3. The apparatus as claimed in claim 1, wherein:
   said at least one transducer unit is arranged and clamped between a membrane and a yoke; and
   said housing element to be compensated is a housing section parallel to the imaginary axis between said membrane and a bearing region of said yoke on said housing.

4. The apparatus as claimed in claim 1, wherein:
   said at least one equalizing element is arranged along the imaginary axis between the at least two housing elements, between which said at least one transducer unit is arranged.

5. The apparatus as claimed in claim 1, wherein:
   said at least one transducer unit is embodied as a stack, which has at least one piezoelectric element.

6. The apparatus as claimed in claim 1, wherein:
   at least one insulating element is provided.

7. The apparatus as claimed in claim 1, wherein:
   said at least one transducer unit has at least one soldering tab.

8. An apparatus for determining and/or monitoring at least one process variable of a medium, comprising:
   at least one housing;
   at least one mechanically oscillatable unit;
   at least one transducer unit, which excites said at least one mechanically oscillatable unit to execute mechanical oscillations, and which receives mechanical oscillations from said at least one mechanically oscillatable unit; and:
   at least one equalizing element, wherein:
   said at least one transducer unit is arranged and clamped between said at least two clamping elements of said at least one housing in such a manner that, at least along an imaginary axis, a predeterminable pressure acts on said at least one transducer unit;
   a coefficient of thermal expansion of said at least one equalizing element and/or a height of said at least one equalizing element along the imaginary axis are/is selected in such a manner that a temperature-expansion of said at least one equalizing element along the imaginary axis during a temperature-related expansion (along the imaginary axis) of a housing element to be compensated leads to the fact that pressure acting along the imaginary axis on said transducer unit is essentially greater than or equal to a predeterminable prestress limit value;

the temperature-related expansion (along the imaginary axis) of said housing element to be compensated affects distance along the imaginary axis between two housing elements, between which said at least one transducer unit is arranged and clamped; and the coefficient of thermal expansion of said at least one equalizing element equal to or greater than the coefficient of thermal expansion of said housing element to be compensated.

9. An apparatus for determining and/or monitoring at least one process variable of a medium, comprising:

at least one housing;

at least one mechanically oscillatable unit;

at least one transducer unit, which excites said at least one mechanically oscillatable unit to execute mechanical oscillations, and which receives mechanical oscillations from said at least one mechanically oscillatable unit; and:

at least one equalizing element, wherein:

said at least one transducer unit is arranged and clamped between said at least two clamping elements of said at least one housing in such a manner that, at least along an imaginary axis, a predeterminable pressure acts on said at least one transducer unit;

a coefficient of thermal expansion of said at least one equalizing element and/or a height of said at least one equalizing element along the imaginary axis are/is selected in such a manner that a temperature-expansion of said at least one equalizing element along the imaginary axis during a temperature-related expansion (along the imaginary axis) of a housing element to be compensated leads to the fact that pressure acting along the imaginary axis on said transducer unit is essentially greater than or equal to a predeterminable prestress limit value;

the temperature-related expansion (along the imaginary axis) of said housing element to be compensated affects distance along the imaginary axis between two housing elements, between which said at least one transducer unit is arranged and clamped; and the height of said at least one equalizing element along the imaginary axis is essentially given by the following formula:

$$HE = HT * \frac{\alpha 1 - \alpha T}{\alpha E - \alpha 1},$$

where HE is height of said at least one equalizing element along the imaginary axis, HT is height of said at least one transducer unit along the imaginary axis, $\alpha 1$ is coefficient of thermal expansion of said housing element to be compensated, $\alpha T$ is coefficient of thermal expansion of said at least one transducer element, and $\alpha E$ is coefficient of thermal expansion of said at least one equalizing element.

10. An apparatus for determining and/or monitoring at least one process variable of a medium, comprising:

at least one housing;

at least one mechanically oscillatable unit;

at least one transducer unit, which excites said at least one mechanically oscillatable unit to execute mechanical oscillations, and which receives mechanical oscillations from said at least one mechanically oscillatable unit; and:

at least one equalizing element, wherein:

said at least one transducer unit is arranged and clamped between said at least two clamping elements of said at least one housing in such a manner that, at least along an imaginary axis, a predeterminable pressure acts on said at least one transducer unit;

a coefficient of thermal expansion of said at least one equalizing element and/or a height of said at least one equalizing element along the imaginary axis are/is selected in such a manner that a temperature-expansion of said at least one equalizing element along the imaginary axis during a temperature-related expansion (along the imaginary axis) of a housing element to be compensated leads to the fact that pressure acting along the imaginary axis on said transducer unit is essentially greater than or equal to a predeterminable prestress limit value;

the temperature-related expansion (along the imaginary axis) of said housing element to be compensated affects distance along the imaginary axis between two housing elements, between which said at least one transducer unit is arranged and clamped; and said at least one transducer unit has at least one soldering tab;

the height of said at least one equalizing element along the imaginary axis is essentially given by the following formula:

$$HE = \frac{(HP + HI + HS) * \alpha 1 - (HP * \alpha P + HI * \alpha I + HS * \alpha S)}{\alpha E - \alpha 1},$$

where HE is height of said at least one equalizing element along the imaginary axis, HP is height of said at least one piezoelectric element along the imaginary axis, HI is height of said at least one insulating element along the imaginary axis, HS is height of said at least one soldering tab along the imaginary axis, $\alpha 1$ is coefficient of thermal expansion of said housing element to be compensated, $\alpha P$ is coefficient of thermal expansion of said at least one piezoelectric element, $\alpha I$ is coefficient of thermal expansion of said at least one insulating element, $\alpha S$ is coefficient of thermal expansion of said at least one soldering tab, and $\alpha E$ is coefficient of thermal expansion of said at least one equalizing element.

* * * * *